United States Patent
Schmidt et al.

(12)

(10) Patent No.: US 6,270,976 B1
(45) Date of Patent: Aug. 7, 2001

(54) CHARACTERIZING NUCLEIC ACID BY MASS SPECTROMETRY

(75) Inventors: Gunter Schmidt, Houghton; Andrew Hugin Thompson, Ayr, both of (GB)

(73) Assignee: Brax Group Limited, Cambridge (GB)

( * ) Notice: Subject to any disclaimer, the term of this patent is extended or adjusted under 35 U.S.C. 154(b) by 0 days.

(21) Appl. No.: 09/508,584

(22) PCT Filed: Sep. 15, 1998

(86) PCT No.: PCT/GB98/02789

§ 371 Date: May 4, 2000

§ 102(e) Date: May 4, 2000

(87) PCT Pub. No.: WO99/14362

PCT Pub. Date: Mar. 25, 1999

(51) Int. Cl.[7] .............................. C12Q 1/68; C12P 19/34; C07H 21/04

(52) U.S. Cl. ............................ 435/6; 435/91.1; 436/173; 536/23.1

(58) Field of Search ...................... 435/6, 91.1; 436/173; 536/23.1

(56) References Cited

FOREIGN PATENT DOCUMENTS

| 94/16101 | * 7/1994 | (WO) | ........................................ 1/68 |
|---|---|---|---|
| WO 94/21822 | 9/1994 | (WO) | . |
| WO 96/27681 | 9/1996 | (WO) | . |
| 97/27331 | * 7/1997 | (WO) | ........................................ 1/68 |
| WO 97/33000 | 9/1997 | (WO) | . |
| WO 97/37041 | 10/1997 | (WO) | . |
| WO 98/15652 | 4/1998 | (WO) | . |
| WO 98/26095 | 6/1998 | (WO) | . |
| WO 98/31830 | 7/1998 | (WO) | . |

OTHER PUBLICATIONS

Britt et al., Journal of Mass Spectrometry, vol. 31, No. 6, 1996, pp. 661–668, XP002088535.
Köster et al., Nature Biotechnology, vol. 14, 1996, pp. 1123–1128, XP002088536.

* cited by examiner

*Primary Examiner*—Jeffrey Fredman
*Assistant Examiner*—Jeanine Goldberg
(74) *Attorney, Agent, or Firm*—Burns, Doane, Swecker & Mathis, L.L.P.

(57) ABSTRACT

The present invention provides a method for analyzing a population of nucleic acid fragments each labeled with a mass label, which method comprises: i) ionizing the population; ii) sorting the ionized population in a mass spectrometer according to mass into sub-populations each containing at least one labeled fragment; iii) cleaving each sub-population to release the mass label associated with each labeled fragment; iv) determining the mass of each released mass label by mass spectroscopy; and v) assigning each mass label to its associated fragment.

16 Claims, No Drawings

CHARACTERIZING NUCLEIC ACID BY MASS SPECTROMETRY

CROSS-REFERENCE TO RELATED APPLICATIONS

This application is a 371 of PCT/GB98/02789, filed on Sep. 15, 1998.

FIELD OF THE INVENTION

This invention concerns a method for analysing nucleic acid. The method is advantageous, since it allows a population of differing nucleic acid fragments to be analysed simultaneously.

BACKGROUND OF THE INVENTION

Methods of single step determination of the mass of nucleic acids in the mass spectrometer have been developed mainly for sequencing (H. Koster et al., Nature Biotechnology 14, 1123–1128, 1996). There are, however, a number of problems with the direct analysis of DNA in a mass spectrometer at present. One is fragmentation of the DNA. The longer a molecule to be analysed is, the greater the degree of fragmentation. This gives rise to mass spectra that are very difficult to interpret. However improvements are envisaged, using modified nucleotide analogues that are resistant to fragmentation within a mass spectrometer.

A further problem of great significance is accurate mass measurement of moderately large biomolecules. This resolution problem limits read lengths of DNA sequences achievable to a significant degree. At present the absolute limit on direct mass analysis of Sanger ladders is determination of sequences of about 100 bases in length and is nearer 30 to 40 bases for practical purposes.

GB 9719284.3 describes the use of nucleic acid hybridisation probes cleavably linked to mass labels for the analysis of nucleic acids. GB 9719284.3 describes a method of sequencing nucleic acids exploiting mass labelled sequencing primers or nucleotides to generate Sanger ladders. This sequencing method uses capillary electrophoresis mass spectrometry as the mass spectrometry method to analyse the mass labelled Sanger ladders generated. These methods require a two-stage analysis; a sizing step which determines the lengths of each nucleic acid in a population, i.e. the number of nucleotides that comprise its linear sequence, followed by identification of the mass label each nucleic acid carries.

BRIEF SUMMARY OF THE INVENTION

The present invention provides a method for analysing a population of nucleic acid fragments each labelled with a mass label, which method comprises:
(i) ionising the population;
(ii) sorting the ionised population in a mass spectrometer according to mass into sub-populations each containing at least one labelled fragment;
(iii) cleaving each sub-population to release the mass label associated with each labelled fragment;
(iv) determining the mass of each released mass label by mass spectroscopy; and
(v) assigning each mass label to its associated fragment.

The population of nucleic acid fragments may be ionised by any suitable method. Electrospray ionisation is particularly useful because it enables direct ionisation from a solution of labelled nucleic acid fragments.

The subsequent steps of sorting the ionised population, cleaving each sub-population and determining the mass of each released mass label may be performed in specified zones of a mass spectrometer. Alternatively, in certain mass spectrometer configurations such as those found in ion trap mass spectrometers or Fourier Transform ion cyclotron resonance spectrometers, the steps of sorting, cleaving and determining the mass of each released mass label are separated temporally but take place in the same "zone".

The step of sorting the ionised population may be effected by the application of a magnetic field, preferably an electromagnetic field such as from a quadrupole, hexapole or dodecapole. Alternatively, the step of sorting the ionised population may be effected by an ion trap or an ion cyclotron device. It is possible to combine electric and magnetic fields in order to perform the sorting step. The step of cleaving each sub-population may be performed in a cleavage zone by collision or by photo-cleavage, for example using a laser. A choice of how to perform the cleaving steps depends to some extent on how the mass label is linked to its associated fragment. The mass label would typically be linked to its associated fragment by a cleavable linker, which could be photo-cleavable or simply designed to cleave automatically upon collision with a concentration of gas phase or with a solid surface in the mass spectrometer.

In the step of determining the mass of each released mass label by mass spectroscopy any suitable mass analyser configuration may be used. This step typically involves separation of the released mass labels from one another followed by detection. The separation may be achieved by any means used in a mass analyser such as a magnetic field, preferably an electromagnetic field including a quadrupole, hexapole or dodecapole. Alternatively, it is possible to use a time of flight configuration to separate the released mass labels from one another. Detection may be effected by any suitable means.

In a preferred arrangement, the nucleic acid fragments and/or mass labels are fragmentation resistant.

In one embodiment, the population of nucleic acid fragments is produced from a method of DNA sequencing such as disclosed in GB 9719284.3. In such a method, a template strand of DNA, typically a primed template, is contacted with nucleotides in the presence of DNA polymerase to produce a series of fragments containing all possible lengths of a strand of DNA complementary to the template strand of DNA. Thus, the population of nucleic acid fragments for analysis comprises the series of fragments. Typically, each fragment is terminated with a nucleotide which is cleavably attached to a corresponding mass label uniquely resolvable in mass spectrometry for identifying the nucleotide. By sorting the ionised population comprising the series of fragments according to mass, the respective length of each member of the series can be determined and/or related to the nucleotide. This enables the sequence of the strand of DNA to be determined.

A further embodiment of this invention employs a modification of the conventional Sanger sequencing strategy that involves degradation of a phosphorothioate containing DNA fragment. This sequencing method utilises alpha-thio dNTPs instead of the ddNTPs used in a conventional Sanger sequencing reaction. These are included with the normal dNTPs in a primer extension reaction mediated by a DNA polymerase. The four sets of base terminating ladders is obtained by including one of the 4 alpha-thio dNTPs in 4 amplification reactions followed by limited digestion with exonuclease III or snake venom phosphodiesterase. (Labeit et al., DNA 5, 173–177, 1986; Amersham, PCT-Application GB86/00349; Eckstein et al., Nucleic Acids Research 16, 9947, 1988). Rather than labelling the primers or the alpha-thio dNTPs with a radioisotope, as disclosed in these previous documents, a mass label is used to identify each ladder and the resultant ladders are analysed by tandem mass spectrometry in this embodiment.

This method of sequencing is advantageous as it favours the formation of the higher molecular weight termination species. The conventional Sanger sequencing methodology, in contrast, generates exponentially less of each termination fragment as the length of the fragment increases. Mass spectrometers are less sensitive to the higher molecular weight species, thus a sequencing method that increases their concentration will improve the sensitivity of the mass spectrometry analysis of these fragments.

In a preferred embodiment the population of nucleic acid fragments is provided on a chip, typically a glass chip, whereby each member of the population is present at a discrete location on the chip. The chip may be treated with a MALDI matrix material. The fragments may be desorbed by applying laser light so as to ionise the population. In this way, fragments, or groups of fragments, located at discrete regions on the chip may be selectively desorbed from the chip by appropriate spatial addressing of the laser light. Laser desorption of fragments may typically be effected in an evacuated chamber which may be integral with the mass spectrometer.

DETAILED DESCRIPTION OF THE INVENTION

This invention describes the use of Tandem Mass Spectrometry techniques as a detection method for nucleic acid sequencing and for other nucleic acid sizing assays that use cleavable mass labels. Capillary electrophoresis mass spectrometry uses a capillary electrophoresis separation to determine the lengths of nucleic acids in a population followed by ionisation of the eluent from the capillary electrophoresis separation and cleavage of the mass labels from the nucleic acids which are then analysed by mass spectrometry. The same size separation, label cleavage and label analysis steps can be performed in a tandem mass spectrometer. Tandem Mass spectrometry describes a variety of techniques where the components of an ion stream pass through more than one mass analysis step. For the purposes of this invention multiple mass labelled nucleic acids can be separated by length in the first mass analyser of a tandem configuration. This is followed by cleavage of mass labels from their associated nucleic acid between the first and second mass analyser. The cleaved mass labels are finally analysed in the second mass analysis stage of the instrument.

The tandem mass spectrometry approach is very desirable as such separations can take place in fractions of seconds rather than in the order of tens of minutes to an hour for a capillary electrophoresis mass spectrometry separation. Thus one can anticipate, further orders of magnitude improvements in sequencing capacity in such a system over that described in PCT/GB98/02048. Capillary electrophoresis based methods face the same problems as gel electrophoresis based separation systems for sizing of nucleic acids although the problems are much more controllable in a capillary system. These problems include band-broadening due to temperature effects, compressions due to secondary structure in the template nucleic acids and inhomogeneities in the separation gels. Determination of the mass of a nucleic acid molecule, even at a low resolution to determine its length will avoid these problems.

The problems associated with methods that exploit direct analysis of DNA molecules by mass spectrometry can be overcome by this invention. The problem of complex spectra due to fragmentation can be partially solved by improved fragmentation resistant analogues of DNA but further improvement is achievable with mass labelled molecules. Mass labels can be chosen to take a different charge to DNA in the mass spectrometer. This means that after cleavage of labels from their corresponding DNA molecule, labels can be exclusively selected for analysis in the second mass analyser by using the appropriate mode of analysis. DNA tends to form ions with a net positive charge, so negative ion mode is generally more effective. Further selectivity is possible if scanning mass analysers, such as quadrupoles, are used for the second mass analysis component as these can filter out any fragment noise. Since labels are well-characterised molecules, picking up a signal from these is greatly simplified in a tandem analysis. Since ionisation is essentially a statistical process, there will be a small background noise of labels from DNA fragmentation products carrying labels though. However by modifying the energy imparted to ions, one can potentially favour the formation of neutral labelled fragments which will not appear in any spectrum. Alternatively one can simply choose mass labels that adopt the same charge as their corresponding DNA molecule but whose peaks in the mass spectrum do not coincide with DNA fragmentation products.

This invention offers improvements over present techniques with regard to these problems. The mass resolution problem is particularly acute for sequencing by single stage mass spectrometry as the length of a DNA ladder and its terminating base are determined by accurate measurement of the mass of the molecule, which requires mass accuracy approaching a single dalton. This invention proposes a tandem scheme where the first mass analyser determines the length of the DNA ladder, which has a mass resolution requirement of the order of 300 daltons followed by cleavage of a label identifying the terminating base in a collision chamber, or another induced fragmentation step. The cleaved label is identified subsequently in the second mass analyser. Labels can be small molecules and can be analysed at high resolution in the second mass spectrometer.

An advantageous embodiment of this technology is the use of fluorinated mass labels when high resolution mass analysis of labels is employed after cleavage from their nucleic acid. A hydrogenated molecule whose integral mass is 100, will have a fractionally higher real mass when measured at very high resolution. In contrast a fluorinated molecule whose integral mass is 100 will tend to have a fractionally lower real mass. These differences in mass are distinguishable in a high accuracy mass analysis and two molecules with the same integral mass but different compositions will produce distinct peaks in the mass spectrum if they have different degrees of hydrogenation and fluorination. Since fluorinated molecules are not common in living systems, this means that a fluorinated mass label will be distinguishable in the mass spectrum even in the presence of contaminating peaks due to fragmentation or buffers as long as the nucleic acids and reagents used are not fluorinated.

An important feature of the invention is the mechanism of cleavage of the labels from a mass labelled nucleic acid which occurs after the first mass analysis step. Collision induced dissociation of labels from their corresponding DNA is one method of cleavage currently used for peptide sequencing. An alternative method would be photon induced cleavage of the mass label from its DNA.

From the point of view of instrumentation, tandem mass spectrometers typically have a linear configuration in which a separate component performs each step of the process and the ion stream is directed from one component to the next. Multiple configurations of linear instruments are possible as discussed later. Certain instruments, however, such as ion trap instruments and fourier transform ion cyclotron mass spectrometers, permit all these steps to occur in a single component.

Sizing Applications of Tandem MS of Mass Labelled Nucleic Acids

A variety of sizing assays based on labelling nucleic acids is applicable with this technology. DNA sizing assays that are compatible with capillary electrophoresis mass spectrometry as discussed in PCT/US97/01046 are equally applicable to Tandem Mass Spectrometry applications. These include but are not limited to differential display, restriction fragment length polymorphism analysis, and linkage analysis.

DNA sizing methods described in earlier patents that are also compatible with tandem MS.
GB9714715.1
GB9707980.0
GB9714716.9.

This invention is highly advantageous for high throughput analysis of mass labelled DNA molecules as it permits very rapid analysis of those molecules. Furthermore, this invention permits multiplexing of a number of labelled nucleic acids. The degree of multiplexing is limited only by the number of mass labels available and resolvable in the mass spectrometer.

Multiplexing Sanger Ladder Detection

Given a large number of mass labels one can multiplex the analysis of a series of Sanger sequencing reactions. One can analyse Sanger ladders derived from different templates simultaneously as long as their terminating bases are labelled with a discrete set of labels or they are identifiable by uniquely labelled primers. Multiplexed Sanger ladders may be generated simultaneously in the same reaction or in spatially discrete reactions followed by pooling of templates depending on the format used.

Labelled Nucleotides

One can label the 4 terminating nucleotides with a different set of 4 mass labels in each reaction that is to be multiplexed. In the simplest scenario one must spatially separate each template and its corresponding labels. Each sequencing reaction would be performed separately and then all the templates would be combined at the end of the sequencing reactions. The Sanger ladders generated are then all separated together in a tandem mass spectrometer, using one of the soft ionisation techniques described below. Each set of 4 mass labels then correlates to a single source template.

This approach is necessary if RNA polymerases are used in conjunction with ribonucleotides or their analogues since most RNA polymerases use promoter sequences rather than primers and so incorporation of labels would have to be effected via labelled nucleotides.

The use of labelled nucleotides is a favourable embodiment in that it avoids certain potential problems associated with primer labelled sequencing. Polymerase reactions often terminate prematurely, without the intervention of blocked nucleotides. This is a problem with primer labelled sequencing because the premature termination generates a background of labelled fragments that are terminated incorrectly. Labelling the blocking nucleotides ensures only correctly terminated fragments are labelled so only these are detected by the mass spectrometer. This then permits cycle sequencing where multiple rounds of primer are add to the template. The sequencing reaction is performed using a thermostable polymerase. After each reaction the mixture is heat denatured and more primer is allowed to anneal with the template. The polymerase reaction is repeated when primer template complexes reform. Multiple repetition of this process gives a linear amplification of the signal, enhancing the reliability and quality of the sequence generated. This an advantage over direct mass analysis techniques which must deal with prematurely terminated products which will appear in the mass spectrum and may result in incorrect base calls.

One can clearly use labelled primers as well, but this requires that each template be sequenced separately in four reactions, one for each terminator which is less advantageous except for multiplexing numerous templates in the same reactions which is discussed below.

Preparation of Templates with Unique Primers or Promoters

In order to permit simultaneous sequencing reactions with mass labels one requires that the Sanger ladder generated for each template be distinguishable from those generated from other templates. This can be achieved using uniquely labelled sequencing primers for each template. In order to ensure that each template bears a unique sequencing primer site one could conceivably engineer a family cloning vectors that bear different primer sequences flanking the integration site for the exogenous DNA to be sequenced. Each sequencing reaction would be performed on a group of templates where only one template derived from each vector type is present so that all the templates in a reaction bear unique primers.

Adapters to Introduce Primers to Restriction Fragments

One can, however, exploit the ability to sequence numerous templates simultaneously to cut out sub-cloning steps in a sequencing project. Consider a large DNA fragment such as a mitochondrial genome or a cosmid. One can cleave such a large molecule with a frequently cutting restriction enzyme to generate fragments of the order of a few hundred bases in length. If one uses a restriction endonuclease like Sau3A1 one is left with fragments with a known sticky end to which one can ligate adapters bearing a known primer sequence.

The majority of properly restricted fragments should as a result bear an adapter at each of their termini. This permits amplification of the adapted restriction fragments at this stage if that is desired. After adaptering and any amplification, one denatures the adapted fragments and hybridises these fragments to a 'capture' primer. The capture primer could be biotinylated and presented to the adapted fragments free in solution, after which captured fragments can be immobilised onto a solid phase support derivitised with avidin. Alternatively the primer could be immobilised onto a solid phase support prior to exposure to the adapted restriction fragments. At this stage one would divide one's template into four separate pools in order to sequence each pool with a different terminating nucleotide.

The captured fragments are made double stranded at this stage by reaction with a polymerase. This means that immobilised Copies of all sequences should be present. The hybridised captured strand can be melted off at this stage and be disposed of if that is desired. One can also amplify the sequence present at this stage by further hybridisation with capture primer.

After denaturing free DNA from the immobilised copies of the template and disposing of free DNA, one can add a series of 'sequencing' primers to the reaction. These primers bear the primer sequence in the adapter and the restriction site by which the adapters were originally ligated to the DNA and an additional overlap of a predetermined number of bases. If one has 64 labels available the overlap can be 3 bases. Each of the possible 3 base overlaps can be identified by a unique mass label. Given a population of the order of 50 to 60 templates one would expect the majority to have a different 3-mer adjacent to the ligated primer. Thus the majority of templates will be expected to hybridise to a distinct primer. Any template that bears a 3-mer immediately adjacent to the adapter that is the same as that on another template would only be resolvable if one is able to determine by the quantity of each template which template to assign a base call to.

With the majority of templates primed with a unique primer one can add polymerase, nucleotide triphosphates and one of the four blocking nucleotides to each reaction and can generate Sanger ladders. If a thermostable polymerase is used, then the ladders can be denatured at the end of each cycle and fresh primers can be added. If cycle sequencing is used then one would almost certainly want some means to select for properly terminated fragments since cycle sequencing not only amplifies the number of properly terminated fragments but also the number of improperly terminated fragments.

The Sanger ladders from each of the four sequencing reactions are then preferably pooled and analysed together by ES tandem mass spectrometry so as to avoid any ambiguities in assigning bases due to experimental differences. Each pool of templates would thus have to have its primers labelled with a unique set of mass labels. Thus a total of 256 mass labels would be required. Each primer thus has four labels, one four each terminator reaction. The labels assigned to each primer should be close in mass and size to minimise differences in migration between each termination reaction.

This approach is appropriate for use with DNA analogues which use a DNA polymerase and a primer sequences.

Multiplexing with Nucleotide Labelled Reactions

A further embodiment of this invention is generating multiple template ladders simultaneously in the same reactions with labelled nucleotides.

Consider a reaction in which unmodified ATP, CTP, GTP and TTP are present with the four corresponding uniquely mass labelled terminating nucleotides. One can generate Sanger ladders for a number of templates simultaneously in the same reaction vessel. If these different templates share a common sequence, either the sequencing primer or a length of sequence after the RNA polymerase that is common to all templates, they can be subsequently sorted into separate groups prior to separation on the basis of the sequence immediately adjacent to the common sequence. One could separate the fragments onto a hybridisation array where the array bears a sequence complementary to the common sequence at all points and an additional predetermined number of bases, N, such that each location on the array bears just one of the possible N base sequences. This means if N is 4 there would be 256 discrete locations on the array. It is expected that a group of templates would in most cases have distinct sequences immediately adjacent to the primer.

This would be an expensive exercise for sorting templates from just one reaction vessel. With a large number of mass labels, however, one can have distinct sets of 4 mass labels identifying blocking nucleotides in a large number of reactions. Thus multiple templates can be added to different reaction vessels, preferably different templates to each reaction vessel. After generating Sanger ladders in each vessel, the reactions can be pooled and the templates from each reaction can be sorted simultaneously. One would expect the majority of ladders of each template from each reaction to segregate to discrete locations on an array and that each location on the array would receive template ladders from a number of distinct reactions.

Alternatively different primers can be linked to a 'sorting sequence', a length of oligonucleotide that could be used to sort ladders with different primers onto a hybridisation chip. Such sorting sequences would ideally be non-complementary to each other to prevent cross hybridisation with each other and should minimally cross-hybridise with the complementary sequences of all other sorting sequences. A full discussion of minimally cross-hybridising sets of oligonucleotides is discussed in PCT/US95/12678. A series of sequencing templates identified by different primers linked to distinct sorting sequences can be used to generate Sanger ladders in the same reaction with the same labelled nucleotide terminators. The resultant Sanger ladders can then be sorted onto a hybridisation array comprising the sequences complementary to the sorting sequences so that each Sanger ladder identified by a particular primer can be sorted to a discrete location on the array.

Having sorted ladders to discrete locations on an array one needs to separate the ladders from each location and identify the mass labels that terminate each set of fragments of each length. How one does this would depend on the array used.

Practically speaking a hybridisation array could comprise an array of wells on microtitre plates, for example, such that each well contains a single immobilised oligonucleotide that is a member of the array. In this situation a sample of the pooled reactions is added to each well and allowed to hybridise to the immobilised oligonucleotide present in the well. After a predetermined time the unhybridised DNA is washed away. The hybridised DNA can then be melted of the capture oligonucleotide and injected into an electrospray interface to a tandem mass spectrometer.

Equally, and preferably, the array could be synthesised combinatorially on a glass 'chip' according to the methodology of Southern or that of Affymetrix, Santa Clara, Calif., or using related ink-jet technologies such that discrete locations on the glass chip are derivitised with one member of the hybridisation array. (A. C. Pease et al. Proc. Natl. Acad. Sci. USA. 91, 5022–5206, 1994. According to South method: U. Maskos and E. M. Southern, Nucleic Acids Research 21, 2269–2270, 1993. E. M. Southern et al, Nucleic Acids Research 22, 1368–1373, 1994). One could hybridise the pooled Sanger ladders to the chip and wash away unhybridised material. The chip can then be treated with a MALDI matrix material such as 3-hydroxypicolinic acid. Having prepared the chip in this way it can be loaded into a MALDI based tandem mass spectrometer and Sanger ladders from discrete locations on the array can be desorbed by application of laser light to the desired location on the array. Direct desorption of DNA from a hybridisation matrix has been demonstrated by Köster et al. (Nature Biotech. 14, 1123–1128). The length of the fragments can be analysed in the first mass analyser followed by cleavage of labels and analysis of these labels in the second mass analyser.

Again, the advantage of multiplexing and sorting templates is the ability to avoid a number of sub-cloning steps in a large scale sequencing project. One would prepare template as described above for primer labelled multiplexing but at the stage when sequencing primer is added, the primers used would not be mass labelled. If RNA polymerases are to be used then the adaptors would bear a promoter sequence for the polymerase rather than a primer sequence. An additional length of common sequence after the promoter would also be needed for sorting purposes.

One can also use engineered vectors to ensure that each template bears a unique sequencing primer site or a promoter with a unique sequence adjacent to it. One could conceivably engineer a family cloning vectors that bear different primer sequences flanking the integration site for the exogenous DNA to be sequenced. Each sequencing reaction would be performed on a group of templates where only one template derived from each vector type is present so that all the templates in a reaction bear unique primers.

Fragmentation of DNA

The mechanism of fragmentation of nucleic acids in the mass spectrometer is currently thought to involve protonation of the nucleobase, which leads to cleavage of the N-glycosidic bond and consequent loss of the base. This leaves the exposed sugar phosphate backbone exposed and prone to further cleavage resulting in fragmentation of the nucleic acid molecule as a whole. (L. Zhu et al, J. Am. Chem. Soc. 117,6048–6056, 1995).

Various chemical modifications to the sugar and nucleobases have been shown to increase stability of DNA in the mass spectrometer. (Tang, Zhu and Smith, Anal. Chem. 69, 302–312, 1997). Modifications shown to be effective include modifications at the 2'-hydrogen of the deoxyribose sugar ring, where electron withdrawing groups are seen to stabilise the N-glycosidic bond. 2'-hydroxyl and 2'-fluoro groups are seen to partially and almost completely block fragmentation, respectively. 2'-hydroxyl groups give RNA or a nucleic acid with arabinose as the sugar component. These modifications were tested in chemically synthesised oligonucleotides in the reference above. These modified nucleotides are not accepted by currently available enzymes and will probably require engineering of polymerases to accept them but will permit much higher resolution separation in the mass spectrometer of nucleic acid bearing these modifications. This in turn will permit mass labelled Sanger ladders of the sort described here to be separated by direct mass spectrometry with less fragmentation, massively increasing throughput. Other modifications that reduce base loss are N7-deaza modifications of adenine and guanosine groups which are accepted by polymerases. (F, Kirpekar et al, Rapid Commun. Mass Spectrom. 8, 727–730, 1994 and H. Köster et al, Nature Biotechnology 14, 1123–1128, 1996).

It should be noted that the discussion above regarding fragmentation of DNA applies particularly to the use of MALDI techniques in that the protonation mechanism that leads to cleavage is thought to be exacerbated by the matrices used to ionise the nucleic acid, since many of these are moderately acidic compounds such as cinnamic acid derivatives, 2,5-dihydroxybenzoic acid, etc. The matrix 3-hydroxypicolinic acid has been shown to produce less fragmentation than most which improves the potential of MALDI based approach. The mass labelling technology is however also highly compatible with ESI based approaches where buffering agents and control over ionisation conditions might allow reduction of the protonation problem.

The problem of complex spectra due to fragmentation can be partially solved by improved fragmentation resistant analogues of DNA but further improvement is achievable with mass labelled molecules. Mass labels can be chosen to take a different charge to DNA in the mass spectrometer. This means that after cleavage of labels from their corresponding DNA molecule, labels can be exclusively selected for analysis in the second mass analyser. Since only labels are analysed in the second mass analyser, most DNA fragments will not appear in the spectrum, or if the labels bear the same charge as the DNA they can be chosen to have masses that are discrete from DNA fragmentation products allowing them to be easily identified. There will still however be a small background from DNA fragments carrying labels which can also be dealt with to some extent by this invention. Fragmentation of singly charged species, generated by the 'mild' ionisation techniques such as Electrospray, MALDI and FAB, generally results in the formation of a charged fragment and an uncharged fragment.

In positive mass spectrometry this gives:

$$[R_1-R_2\text{-label}]+ \rightarrow R_1^+ + R_2\text{-label} \quad (1)$$

or $$[R_1-R_2\text{-label}]+ \rightarrow R_1 + R_2\text{-label}+ \quad (2)$$

Or alternatively in negative ion spectrometry:

$$[R_1-R_2\text{-label}]- \rightarrow R_1-+R_2\text{-label} \quad (1)$$

or $$[R_1-R_2\text{label}]- \rightarrow R_1 + R_2\text{-label} \quad (2)$$

The DNA fragments without labels, whether charged or not, will not be seen in the second mass analysis phase or should be resolvable from mass label peaks depending on the label used. Uncharged species with labels will also not be seen in the final spectrum. If the fragmentation paths in (1) and (2) are equally likely then clearly, one would expect half the fragmentation noise when compared with the noise seen in direct mass spectrometry of Sanger ladders but the formation of the ions is not equally likely but is determined by the heats of formation of the species involved. Generally the stability of a bond is analysed by comparing the heat of formation of the ion species on the left in the equations above with the heat of formation of the neutral species on the right, as discussed below. For the purposes of sequencing one can label either the 3' terminus, if labelled nucleotide terminators are used, or one can label the 5' terminus, by using labelled primers. One can thus choose the format which minimises noise through favouring fragmentation pathway in equation (1). Furthermore, the fragmentation of molecular ions can to some extent be controlled by determining the energy imparted to the ions in the ionisation process. This is not easy to control in MALDI based techniques which is intrinsically a relatively high energy process, but in electrospray, APCI (Atmospheric Pressure Chemical Ionisation) and FAB based techniques it is relatively easy to control the energy imparted to ions through control of the accelerating potential used.

This analysis is over-simplified but is sufficient to illustrate the principle that mass labels can offer an advantage in avoiding some of the problems with fragmentation. Oligonucleotide fragmentation is a reasonably complicated process and is not fully understood although L. Zhu et al (J. Am. Chem. Soc. 117,6048–6056, 1995) have elucidated a possible mechanism of nucleotide fragmentation in MALDI based systems. The distribution of charge on fragmentation ions was not clearly determinable from their results, however cleavage appears to be favoured at the 3' C—O bond between deoxyribose and the phosphodiester linkage, leaving a phosphate group on the 3' end fragment. For positive ion mode sequencing in the first mass analyser, this may be advantageous as the appearance of a negative ion will not be detected. This would favour nucleotide labelled sequencing over primer labelled sequencing.

RNA Based Sequencing

One possible fragmentation resistant DNA 'analogue' that already has appropriate polymerases is of course RNA. RNA is chemically less stable than DNA but is more resistant to fragmentation in the mass spectrometer. Generally RNA is disliked as a material to work with as it is so easy to contaminate with degrading enzymes in manual experiments. However for automated high throughput sequencing this may not be a significant problem as contamination by RNAses, etc. can be much more rigorously controlled. For use in sequencing one would require terminating ribonucleotides or analogues that are accepted by an RNA polymerase. Such terminators could be generated by synthesising ribonucleotides with the 3' hydroxyl blocked. The blocking group could be a linker to a cleavable mass label identifying the nucleotide.

To avoid the problems of RNA sensitivity to enzymatic degradation, one can use RNA analogues that are resistant to enzymatic degradation and are fragmentation resistant in a mass spectrometer such as 2'-fluoro sugar analogues or 2'-O-methyl sugar analogues. Terminators could be generated as described for ribonucleotides above.

Mass Resolution

The problem of mass resolution faced by direct techniques can be greatly reduced by the use of mass labels.

Charge Carrying Non-cleavable Tags

If one wishes to use mass labels that take a different charge from DNA, one should ensure that the DNA carries the appropriate charge. To be certain one can tag the DNA with a charge carrier that forms the appropriate ion with a very high probability or is already charged prior to ionisation such as quaternary ammonium ions which could be attached by a fragmentation resistant linkage to a sequencing primer.

One might also use multiply charged tags attached to sequencing primers to increase the charge on a DNA molecule so that its mass charge ratio is reduced. This would increase mass resolution by ensuring that higher mass molecules can be analysed in the most sensitive detection range of a given mass spectrometer. Thus a DNA molecule with a mass of the order of 6000 daltons, which is outside the most sensitive range of most instruments, but carrying 3 positive charges will have a mass/charge ratio of about 2000 which falls well into the sensitive range of most mass spectrometers.

Equalisation of Base Masses

Tandem separation of mass labelled Sanger Ladders according to this invention requires that in the first analyser, molecules are separated by length. As mentioned above this has a lower requirement for mass accuracy than conventional approaches. However if a number of labelled templates are to be analysed simultaneously it may be advantageous to normalise base masses, i.e. synthesis nucleotide analogues for adenine, cytosine, guanine and thymine that have the same mass, so that addition of any of the four nucleotides to an oligonucleotide increases its mass by the same amount. This normalisation should allow one to avoid any overlap in masses between labelled molecules of different lengths ensuring that labelled molecules arrive sequentially prior to removal and analysis of the mass label identifying the terminating nucleotide.

Furthermore, if one wishes to use labels with masses greater than the mass of a single nucleotide, normalisation would be beneficial. One could then use a pair of 'calibration ladders' bearing the lightest and heaviest mass labels to demarcate the 'arrival envelope' of labelled molecules of a given length if desired. Such envelopes could overlap for molecules of differing lengths, but as long as any given template is labelled with a set of labels that are close in mass, they will always arrive in the correct order.

Mass Spectrometry Techniques

Present approaches to direct analysis of Sanger ladders tend to favour the use of MALDI TOF instruments. MALDI approaches generally do not induce fragmentation in ions but the acidic matrices used in much DNA work are believed to be responsible for much fragmentation. Thus unless fragmentation resistant DNA analogues are available or better matrices are found this technique will always face this problem. Furthermore TOF instruments are limited in the mass accuracy achievable for high molecular weight species. This is exacerbated by the use of MALDI as an ionisation technique as this generates ions with quite a broad kinetic energy distribution, although this problem can be countered to some extent in reflectron instruments.

Electrospray ionisation produces ions with a very narrow energy distribution. Furthermore it generally does not induce fragmentation in molecular ions. As DNA is presented to the mass spectrometer in solution one can also avoid acid induced fragmentation by using appropriate buffers. Similarly liquid phase based Fast Atom Bombardment ionisation techniques could be used to generate very restricted ion populations. These techniques may be advantageous to improve mass resolution in higher molecular mass species and in reducing fragmentation.

Mass Analyser Geometries

Mass spectrometry is a highly diverse discipline and numerous mass analyser configurations exist and which can often be combined in a variety of geometries to permit analysis of complex organic molecules such as the peptide tags generated with this invention.

Analysis of Mass Labelled Nucleic Acids by Tandem Mass Spectrometry

Tandem mass spectrometry describes a number of techniques in which a ions from a sample are selected by a first mass analyser on the basis of their mass charge ratio for further analysis by induced fragmentation of those selected ions. The fragmentation products are analysed by a second mass analyser. The first mass analyser in a tandem instrument acts as a filter selecting ions to enter the second mass analyser on the basis of their mass charge ratio, such that essentially a species of only a single mass/charge ratio enter the second mass analyser at a time. On leaving the first mass analyser, the selected ion passes through a collision chamber, which results in fragmentation of the molecule.

ION SOURCE→MS1→COLLISION CELL→MS2→ION DETECTOR

If appropriate fragmentation resistant analogues are used and a suitably fragmentation labile linker is used to couple a mass label to a nucleic acid molecule, a mass labelled nucleic acid molecule, or group of molecules, can be separated from other molecules of different length by a relatively low resolution mass filtering step in the first mass analyser. The mass labels on selected species can then be cleaved from the DNA in a collision induced fragmentation step. The labels can then be analysed in the second mass analyser of the tandem instrument.

Various tandem geometries are possible. Conventional 'sector' instruments can be used where the electric sector provide the first mass analyser stage, the magnetic sector provides the second mass analyser, with a collision cell placed between the two sectors. This geometry is not ideal for peptide sequencing. Two complete sector mass analysers separated by a collision cell could be used for analysis of mass labelled nucleic acids. A more typical geometry used is a triple quadrupole where the first quadrupole filters ions for collision. The second quadrupole in a triple quadrupole acts as a collision chamber while the final quadrupole analyses the fragmentation products. This geometry is quite favorable. Another more favorable geometry is a Quadrupole/Orthogonal Time of Flight tandem instrument where the high scanning rate of a quadrupole is coupled to the greater sensitivity of a TOF mass analyser to identify the products of fragmentation.

Ion Traps

Ion Trap mass spectrometers are a relative of the quadrupole spectrometer. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device by collision with trapped ions. Collisions both increase ionisation when a sample is introduced into the trap and damp the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. One can retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

For nucleic acid sequencing and other nucleic acid sizing applications, an ion trap is quite a good instrument. A sample of mass labelled population of nucleic acids can be injected into a spectrometer. For a Sanger ladder, individual 'rungs', can be ejected specifically for cleavage in a collision chamber followed by further analysis in a second mass analyser of a tandem geometry instrument. Alternatively samples of a mass labelled nucleic acid population can be injected into a trap. A single rung of a ladder, i.e. all species falling within about 100 daltons, or a mass labelled tandem satellite repeat linkage marker could be retained and the labels could be removed by collision induced fragmentation. Specific label species can then be scanned for and ejected from the trap for detection.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radiofrequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by fourier transform analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT of signals detected by the 'receiver plates', however the fragment ions can be ejected from the cavity and analysed in a tandem configuration with a quadrupole, for example.

For nucleic acid sequencing and other nucleic acid sizing applications FTICR MS could be used and may be advantageous as these instruments have a very high mass resolution for molecules of significant size.

Mass labels that can be used in the present invention include those disclosed in GB 9700746.2, GB 9718255.4, GB 9726953.4, PCT/GB 98/00127 and the UK application having Page White and Farrer file number 87820. The contents of these applications are incorporated herein by reference.

What is claimed is:

1. A method for analysing a population of nucleic acid fragments each labelled with a mass label, which method comprises:
   (i) Ionising the population;
   (ii) sorting the ionised population in a mass spectrometer according to mass into sub-populations each containing at least one labelled fragment;
   (iii) cleaving each sub-population in a mass spectrometer by collision induced dissociation, to release the mass label associated with each labelled fragment;
   (iv) determining the mass of each released mass label by mass spectroscopy; and
   (v) assigning each mass label to its associated fragment, thereby identifying the nucleic acid fragment.

2. The method according to claim 1, wherein the nucleic acid population is produced by performing a Sanger sequencing reaction on a nucleic acid template.

3. The method according to claim 2, wherein each terminating nucleotide used in the Sanger sequencing reaction comprises a mass label specific to that nucleotide, such that each fragment produced in the Sanger sequencing reaction comprises a mass label specific to the terminal nucleotide of that fragment.

4. The method according to claim 3, wherein the nucleic acid population comprises fragments produced from a plurality of Sanger sequencing reactions carried out on a plurality of nucleic acid templates.

5. The method according to claim 4, wherein the nucleic acid population is produced by pooling the fragments produced from a plurality of separate Sanger sequencing reactions.

6. The method according to claim 5, wherein the set of labels used in each Sanger sequencing reaction is specific to that Sanger sequencing reaction, such that the label set identifies the template of that Sanger sequencing reaction.

7. The method according to claim 4, wherein each of the Sanger sequencing reactions is carried out simultaneously in the same reaction, the templates being identified by sorting the fragments according to the base sequence of the fragments.

8. The method according to claim 2, wherein each Sanger sequencing reaction is carried out using four terminating nucleotides in the same reaction.

9. The method according to claim 2, wherein terminating nucleotides are employed in the Sanger sequencing reaction which comprise ddNTP.

10. The method according to claim 1, wherein the nucleic acid population is produced by subjecting a nucleic acid template to a PCR reaction in the presence of dNTP and alpha-thio-dNTP, to produce a nucleic acid comprising DNTP and alpha-thio NTP, and contacting the resulting nucleic acid with an exonuclease or snake venom phosphodiesterase to degrade the nucleic acid into fragments.

11. The method according to claim 1, wherein each alpha-thio-dNTP used in the PCR reaction comprises a mass label specific to that nucleotide, such that each fragment produced after degradation comprises a mass label specific to the terminal nucleotide of that fragment.

12. The method according to claim 1, wherein the nucleic acid fragments and/or the mass labels are fragmentation resistant.

13. The method according claim 1, wherein the mass labels labelling the nucleic acid fragments are selected such that when subjected to mass spectrometry, the labels take a different charge to the nucleic acid fragments.

14. The method according to claim 1, wherein when subjected to mass spectrometry, the mass labels take a negative charge.

15. The method according to claim 1, wherein the mass labels are fluorinated mass labels.

16. The method according to claim 1, wherein identifying the nucleic acid fragment comprises determining the sequence of the nucleic acid fragment.

* * * * *